United States Patent
Kang et al.

(10) Patent No.: US 9,247,908 B2
(45) Date of Patent: Feb. 2, 2016

(54) PHYSIOLOGICAL DETECTION MODULE

(71) Applicant: KING'S METAL FIBER TECHNOLOGIES CO., LTD., Taichung (TW)

(72) Inventors: Yu-Hsun Kang, Taipei (TW); Hao-Chen Wang, Taipei (TW); Shu-Fen Liao, Taipei (TW)

(73) Assignee: King's Metal Fiber Technologies Co., Ltd., Taichung (TW)

( * ) Notice: Subject to any disclaimer, the term of this patent is extended or adjusted under 35 U.S.C. 154(b) by 152 days.

(21) Appl. No.: 14/098,819

(22) Filed: Dec. 6, 2013

(65) Prior Publication Data

US 2015/0157265 A1 Jun. 11, 2015

(51) Int. Cl.
*A61B 5/04* (2006.01)
*A61B 5/00* (2006.01)
*A61B 5/0408* (2006.01)

(52) U.S. Cl.
CPC ........... *A61B 5/6831* (2013.01); *A61B 5/04085* (2013.01); *A61B 5/6804* (2013.01)

(58) Field of Classification Search
CPC ..................................................... A61B 5/6831
USPC .................. 600/372, 384, 386, 388–390, 394
See application file for complete search history.

(56) References Cited

U.S. PATENT DOCUMENTS

| | | | | |
|---|---|---|---|---|
| 2,318,207 | A * | 5/1943 | Ellis | 600/384 |
| 3,542,010 | A * | 11/1970 | Love | 600/384 |
| 3,967,628 | A * | 7/1976 | Vredenbregt | 607/149 |
| 4,088,133 | A * | 5/1978 | Twentier | 606/32 |
| 4,391,279 | A * | 7/1983 | Stein | 600/387 |
| 5,313,952 | A * | 5/1994 | Hoch | 600/390 |

\* cited by examiner

*Primary Examiner* — Lee S Cohen
(74) *Attorney, Agent, or Firm* — Rosenberg, Klein & Lee

(57) ABSTRACT

A physiological detection module includes a conductive transmission unit, a coupler, and an electrical connector. The coupler is arranged on a surface of the conductive transmission unit. The coupler includes a receiving chamber extending therethrough. The coupler includes a positioning groove circumferentially formed thereon for coupling and positioning. The electrical connector extends through the conductive transmission unit and the receiving chamber of the coupler to connect the conductive transmission unit and the coupler together. As such, a physiological detection module is provided, which can be manufactured separately, is easy to manufacture, can be efficiently assembled for use, is securely coupled, and can prevent short-circuiting.

3 Claims, 6 Drawing Sheets

PHYSIOLOGICAL DETECTION MODULE

FIELD OF THE INVENTION

The present invention relates to a physiological detection module, and in particular to a physiological detection module for use in physiological detection.

BACKGROUND OF THE INVENTION

Nowadays, to detect physiological signals of a human body, such as heart beat and brain wave, a plurality of detection elements of physiological detection equipment is attached to (or put on) various sites on a surface of the human body to allow these detection elements to detect the current that spreads to the peripheral tissues or the body surface occurring when nervous impulses (namely variation of membrane potential) passes through the organs of the human body (such as heart and head). A detected signal is then transmitted by electrical wires from those detection elements to the physiological detection equipment to be processed and converted into data to be displayed. In this way, the condition of an inspected portion (such as heart rate and variation of brain wave) can be realized.

A conventionally used physiological inspection garment or chest band can be used to inspect the condition of an inspected portion. However, their manufacture requires first lapping a piece of cloth that is used to make the physiological inspection garment or the chest band over a conductive fabric and making holes therein, then placing a piece of rubber on the cloth and placing a female button on the rubber piece, and finally penetrating a base pin sequentially through the conductive fabric, the cloth, and the rubber piece to contact the female button to be riveted with the female button to complete the manufacture of the physiological inspection garment or the chest band. All the components must be processed for one time processing and the physiological inspection garment or the chest band cannot be manufactured separately. Thus, the entire structure, after being formed, cannot be changed. It severely affects the convenience of manufacture and flexibility of commercial use.

In view of these problems associated with the use and manufacture of the conventional put-on type physiological inspection garment or chest band, as well as the imperfectness of the structural design thereof, the present invention aims to provide a physiological signal detection module that allows for separate manufacture, and is easy to manufacture, is securely coupled, and can prevent short-circuiting.

SUMMARY OF THE INVENTION

An object of the present invention is to provide a physiological detection module, wherein a combined arrangement of a conductive transmission unit, a coupler, and an electrical connector, with a positioning groove being circumferentially formed on the coupler, is provided, which, in an application to a chest band or a physiological inspection garment 60, allows the physiological detection module of the present invention to be used in combination with two button holes formed in the chest band or the physiological inspection garment by having the positioning grooves of the couplers of two physiological detection modules respectively mounted to the button holes, without additionally providing coupling structures on the chest band or the physiological inspection garment. Further, to change the position where the physiological detection module is mounted to the chest band or the physiological inspection garment, it only needs to provide a button hole in the location where mounting is to be made to allow the physiological detection module of the present invention to be mounted to the chest band or the physiological inspection garment. In this way, the conductive transmission unit, the coupler, and the electrical connector can be conveniently and efficiently assembled and mounted to form a physiological detection module, which can be manufactured separately with respect to the chest band or the physiological inspection garment and can be efficiently assembled for use when desired so as to greatly improve the convenience of manufacture and to enhance the utilization thereof.

Another object of the present invention is to provide a physiological detection module, wherein an electrical connector is formed by coupling a female button and a base pin together and the female button can be set at one end of a receiving chamber of a coupler, while the base pin is set through a conductive transmission unit and the receiving chamber of the coupler to be riveted to the female button, so that practical advantages, such as efficient coupling and positioning and electrical connection with an external device for providing physiological signals, can be achieved.

A further object of the present invention is to provide a physiological detection module, wherein in a use, a water-resistant layer (the water-resistant layer being a plastic film that is mounted through thermal bonding) can be set at the side of a base pin of an electrical connector of one of two physiological detection modules so as to completely shield an end of one of the two physiological detection modules to prevent the two physiological detection modules from short-circuiting and thus improving the safety of use.

To achieve the above objects, the present invention provides a physiological detection module, which comprises a conductive transmission unit, a coupler, and an electrical connector. The coupler is set on a surface of the conductive transmission unit. The coupler comprises a receiving chamber extending therethrough. The coupler also comprises a positioning groove circumferentially formed thereon for coupling and positioning. The electrical connector extends through the conductive transmission unit and the receiving chamber of the coupler to connect the conductive transmission unit and the coupler together. As such, a physiological detection module is provided, which can be manufactured separately, is easy to manufacture, can be efficiently assembled for use, is securely coupled, and can prevent short-circuiting thereby improving the utilization, convenience, and safety thereof.

The physiological detection module discussed above further comprises a water-resistant layer, which is mounted to the conductive transmission unit.

In the physiological detection module discussed above, the electrical connector a female button and a base pin coupled to each other. The female button is set at one end of the receiving chamber of the coupler and the base pin extends through the conductive transmission unit and the receiving chamber of the coupler to couple to the female button.

In the physiological detection module discussed above, the conductive transmission unit comprises a conductive fabric.

BRIEF DESCRIPTION OF THE DRAWINGS

The present invention will be apparent to those skilled in the art by reading the following description of preferred embodiments thereof with reference to the drawings, in which.

DETAILED DESCRIPTION OF THE PREFERRED EMBODIMENTS

Figure 1:
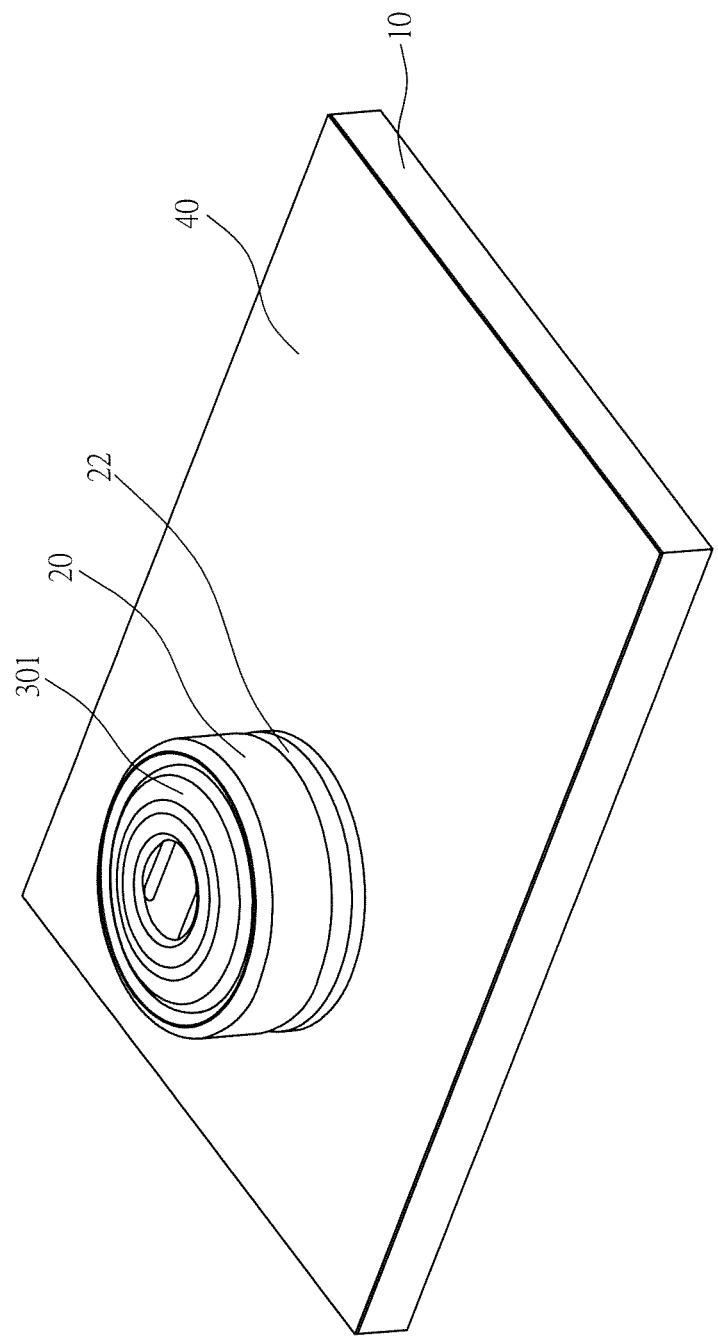
FIG. 1 is a perspective view showing an embodiment of the present invention in an assembled form.
Figure 2:
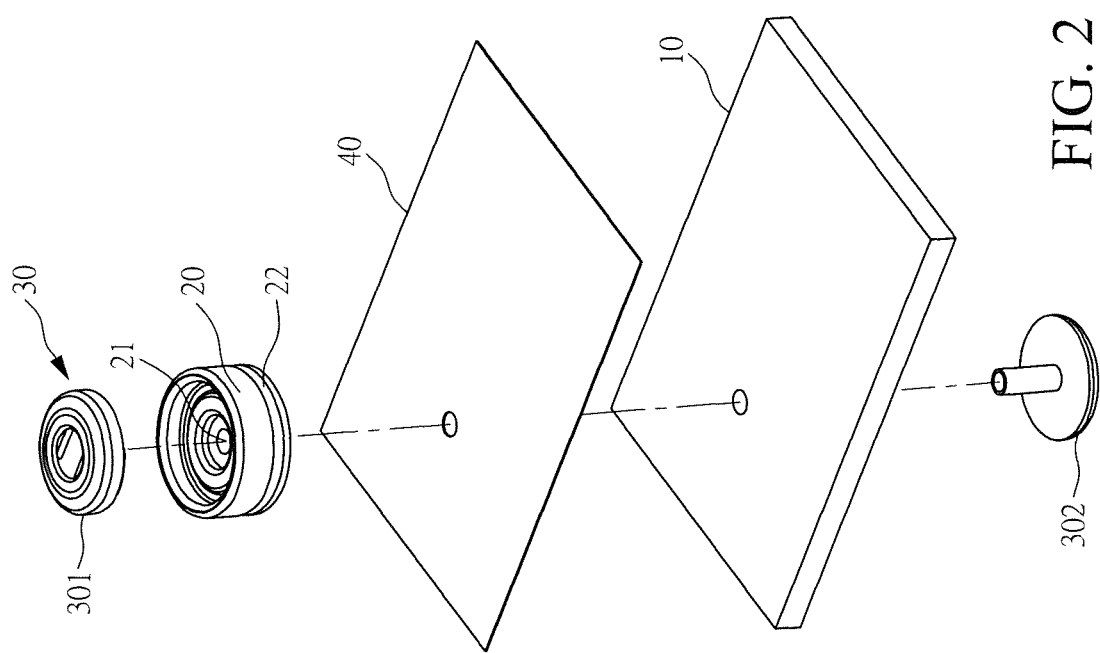
FIG. 2 is an exploded view of the embodiment of the present invention.
Figure 3:
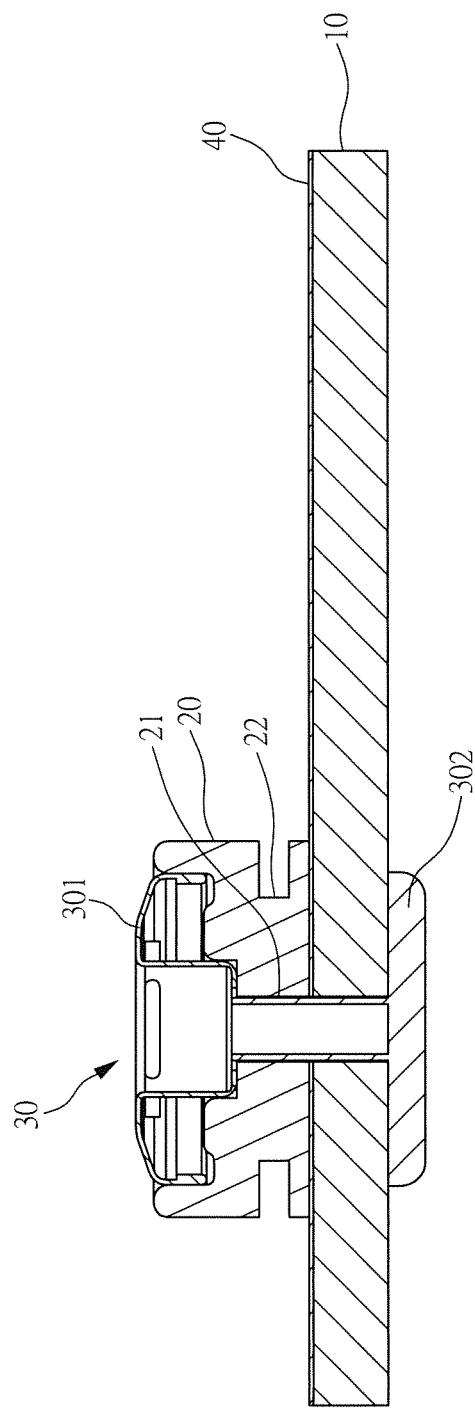
FIG. 3 is a cross-sectional view of the embodiment of the present invention.
Figure 4:
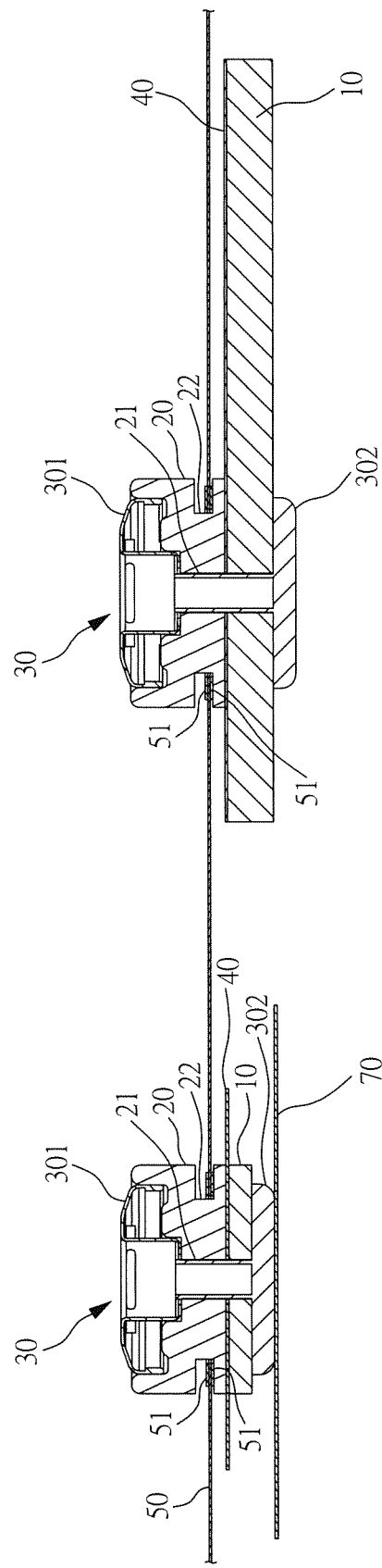
FIG. 4 is a cross-sectional view illustrating a use of the embodiment of the present invention.
Figure 5:
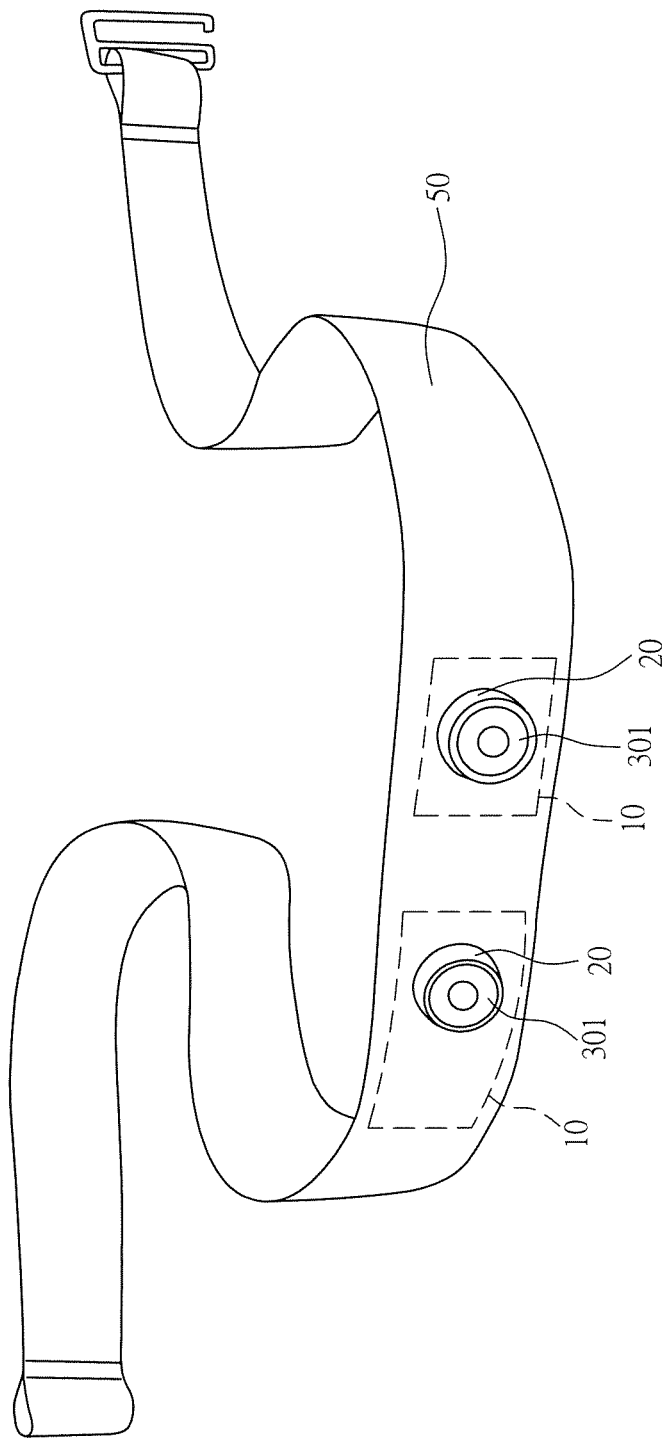
FIG. 5 is a perspective view illustrating a first example of an application of the embodiment of the present invention.
Figure 6:
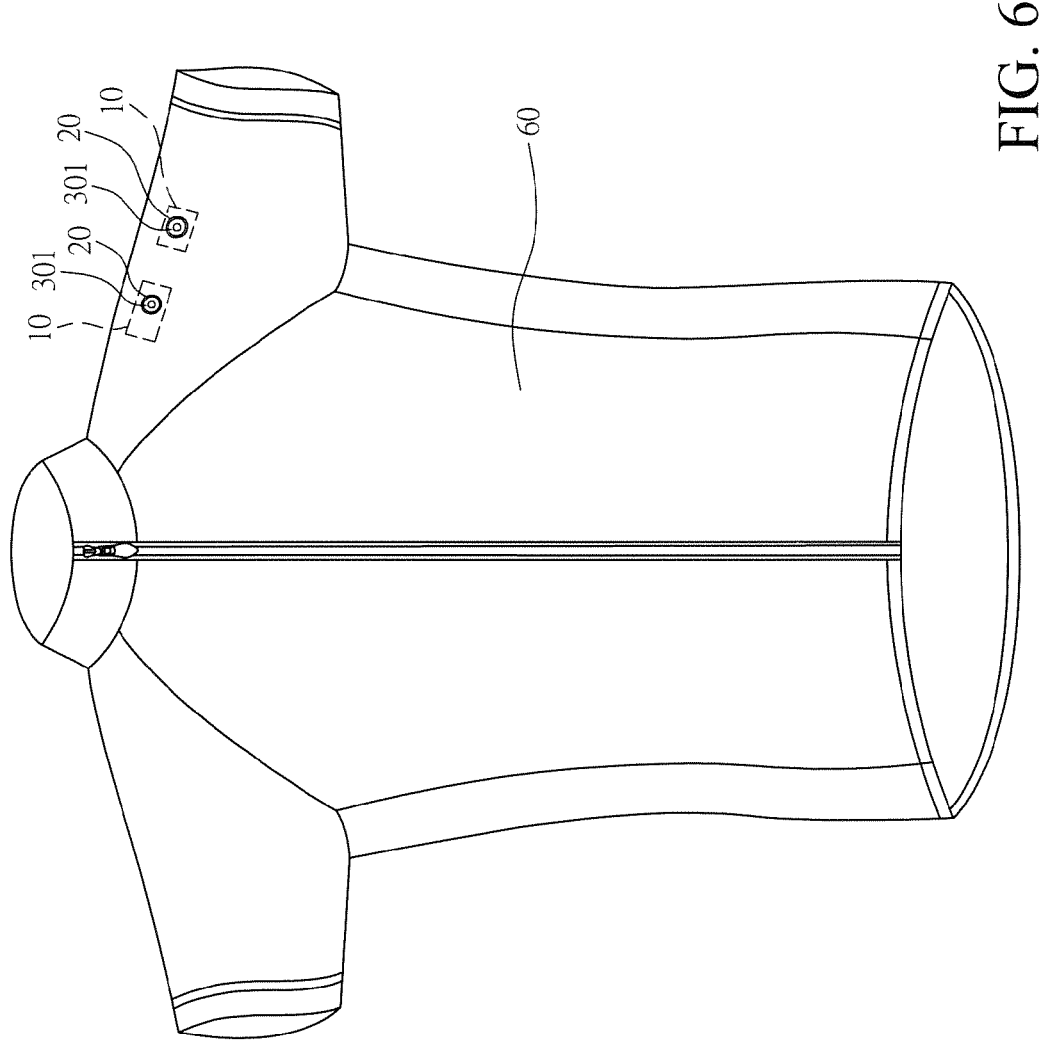
FIG. 6 is a perspective view illustrating a second example of an application of the embodiment of the present invention.

With reference to the drawings and in particular to FIGS. 1-3, the present invention provides a physiological detection module, which comprises a conductive transmission unit 10 (wherein the conductive transmission unit 10 comprises a conductive fabric); a coupler 20, wherein the coupler 20 is arranged on a surface of the conductive transmission unit 10, the coupler 20 comprising a receiving chamber 21 extending therethrough, the coupler 20 comprising a positioning groove 22 circumferentially formed on an outer circumference thereof for purposes of coupling and positioning; and an electrical connector 30, wherein the electrical connector 30 extends through the conductive transmission unit 10 and the receiving chamber 21 of the coupler 20 to connect the conductive transmission unit 10 and the coupler 20 together.

The physiological detection module according to the present invention further comprises a water-resistant layer 40. The water-resistant layer 40 is mounted to the conductive transmission unit 10 to improve water resistance.

The electrical connector 30 comprises a female button 301 and a base pin 302 that are coupled to each other. The female button 301 is arranged at one end of the receiving chamber 21 of the coupler 20 and the base pin 302 extends through the conductive transmission unit 10 and the receiving chamber 21 of the coupler 20 to be riveted to the female button 301.

With the above arrangement, a physiological detection module is provided. Referring to FIGS. 1-6, the features of the present invention are that a combined arrangement of the conductive transmission unit 10, the coupler 20, and the electrical connector 30, with a positioning groove 22 being circumferentially formed on the coupler 20, is provided, which, in an application to a chest band 50 (see FIG. 5) or a physiological inspection garment 60 (see FIG. 6), allows the physiological detection module of the present invention to be used in combination with two button holes formed in the chest band 50 or the physiological inspection garment 60 by having the positioning grooves 22 of the couplers 20 of two physiological detection modules respectively mounted to the button holes (each of the button holes has upper and lower circumferential edges at each of which a positioning member 51 is arranged, each of the positioning members 51 being a plastic film that is attached to the circumferential edge by thermal bonding in order to improve force resistance of the button hole), without additionally providing coupling structures on the chest band 50 or the physiological inspection garment 60. Further, to change the position where the physiological detection module is mounted to the chest band 50 or the physiological inspection garment 60, it only needs to provide a button hole in the location where mounting is to be made to allow the physiological detection module of the present invention to be mounted to the chest band 50 or the physiological inspection garment 60. In this way, the conductive transmission unit 10, the coupler 20, and the electrical connector 30 can be conveniently and efficiently assembled and mounted to form a physiological detection module, which can be manufactured separately with respect to the chest band 50 or the physiological inspection garment 60 and can be efficiently assembled for use when desired so as to greatly improve the convenience of manufacture and to enhance the utilization thereof.

Further, with the electrical connector 30 being formed by coupling a female button 301 and a base pin 302 together, the female button 301 can be set at one end of the receiving chamber 21 of the coupler 20, while the base pin 302 is set through the conductive transmission unit 10 and the receiving chamber 21 of the coupler 20 to be riveted to the female button 301, so that practical advantages, such as efficient coupling and positioning and electrical connection with an external device for providing physiological signals, can be achieved.

Further, in the use of the present invention, a water-resistant layer 70 (the water-resistant layer 70 being a plastic film that is mounted through thermal bonding) can be set at the side of the base pin 302 of the electrical connector 30 of one of the two physiological detection modules so as to completely shield an end of one of the two physiological detection modules to prevent the two physiological detection modules from short-circuiting and thus improving the safety of use.

In summary, the present invention provides a physiological detection module that can be manufactured separately, is easy to manufacture, can be efficiently assembled for use, is securely coupled, and can prevent short-circuiting thereby improving the utilization, convenience, and safety thereof.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A physiological detection module, comprising:
a conductive transmission unit;
a coupler, which is arranged on a surface of the conductive transmission unit, the coupler comprising a receiving chamber extending therethrough, the coupler comprising a positioning groove circumferentially formed thereon for coupling and positioning; and
an electrical connector, which extends through the conductive transmission unit and the receiving chamber of the coupler to connect the conductive transmission unit and the coupler together;
wherein the electrical connector comprises a female button and a base pin coupled to each other, the female button being set at one end of the receiving chamber of the coupler, the base pin extending through the conductive transmission unit and the receiving chamber of the coupler to couple to the female button.

2. The physiological detection module as claimed in claim 1 further comprising a water-resistant layer, which is positioned between the conductive transmission unit and the coupler.

3. The physiological detection module as claimed in claim 1, wherein the conductive transmission unit comprises a conductive fabric.

* * * * *